United States Patent [19]
Honda et al.

[11] Patent Number: 5,637,734
[45] Date of Patent: Jun. 10, 1997

[54] PROCESS FOR PRODUCING L-ASCORBIC ACID

[75] Inventors: Haruomi Honda, Kawanishi; Toru Yamano, Itami; Masayuki Yamashita, Suita, all of Japan

[73] Assignee: Takeda Chemical Industries, Ltd., Osaka, Japan

[21] Appl. No.: 553,027

[22] Filed: Nov. 3, 1995

[30] Foreign Application Priority Data

Nov. 11, 1994 [JP] Japan .................................. 6-277314
Sep. 6, 1995 [JP] Japan .................................. 7-228887

[51] Int. Cl.$^6$ .................................. C07D 307/62
[52] U.S. Cl. .................................. 549/315
[58] Field of Search .................................. 549/315

[56] References Cited

U.S. PATENT DOCUMENTS 5,041,563  8/1991  Fahrni et al. ........................... 549/315

FOREIGN PATENT DOCUMENTS

| 0086324 | 8/1983 | European Pat. Off. . |
| 0324261 | 7/1989 | European Pat. Off. . |
| 48-15931 | 5/1973 | Japan . |
| 466548 | 5/1937 | United Kingdom . |
| 2205567 | 12/1988 | United Kingdom . |

OTHER PUBLICATIONS

Chemical Abstracts, vol. 50, No. 8, Apr. 25, 1956, Columbus, Ohio, US, Abstract No. 5992d, M. Yamazaki et al. "VIII. Formation and isolation of 2-keto-L-gulonic acid from the mixture of calcium L-idonate and calcium D-gluconate by submerged fermentation, and synthesis of vitamin C from 2-keto-L-gulonic acid", *abstract* & J. Agr. Chem. Soc. Japan, vol. 28, 1954, pp. 890–894.

*Primary Examiner*—Bernard Dentz
*Attorney, Agent, or Firm*—Wenderoth, Lind & Ponack

[57] ABSTRACT

A process for producing L-ascorbic acid, which comprises reacting 2-keto-L-gulonic acid with an acid in an ether or an inert organic solvent containing an ether in the presence of water and a surfactant.

7 Claims, No Drawings

PROCESS FOR PRODUCING L-ASCORBIC ACID

BACKGROUND OF THE INVENTION

1. Field of the Invention

The present invention relates to a process for producing L-ascorbic acid, so called vitamin C.

2. Description of Related Art

L-Ascorbic acid has been industrially produced by the process reported by Reichstein and Grüssner (Helv. Chim. Acta., 17, 311–328 (1934)) or improved processes thereof. In these processes, 2-keto-L-gulonic acid is synthesized from D-glucose through many reaction steps, esterified, and reacted with sodium methoxide in methanol to give the corresponding lactone, which is then acidified with hydrogen chloride gas to give L-ascorbic acid. Recently, fermentation processes for producing 2-keto-L-gulonic acid from L-sorbose were found (e.g., JP-A 60-70073), and it has been demanded to establish more advantageous processes for producing L-ascorbic acid from 2-keto-L-gulonic acid.

For example, the following processes for producing L-ascorbic acid from 2-keto-L-gulonic acid have been known: (1) a process comprising reacting 2-keto-L-gulonic acid with conc. hydrochloric acid in an organic solvent (U.S. Pat. No. 2,462,251), (2) a process comprising reacting 2-keto-L-gulonic acid with a mineral acid in the presence of a surfactant in an inert solvent (JP-B 48-15931), (3) a process comprising reacting 2-keto-L-gulonic acid with anhydrous hydrochloric acid gas in an inert solvent in the presence of a surfactant (JP-A 63-500454), etc. However, the above processes do not necessarily provide satisfactory yields of L-ascorbic acid in industrial production. In addition, because the above processes produce a large amount of impurities as by-products responsible for coloration, purification procedures are complicated. Thus, the above processes are not industrially practical.

JP-A 64-79165 discloses a process for producing L-ascorbic acid which comprises reacting 2-keto-L-gulonic acid with an aqueous solution of conc. hydrochloric acid combined with hydrogen chloride gas in the presence of a surfactant in an inert solvent using an aliphatic ketone as a coexisting solvent. This process has achieved a high yield of the desired product by optimizing the amounts of water and hydrochloric acid independently. The presence of aliphatic ketones, which is one of the features of this process, is essential to maintain a high concentration of hydrochloric acid in the reaction system. Aliphatic ketones are, however, decomposed by acid catalysts, and this is a drawback of this process. For example, when acetone is used as an aliphatic ketone, undesirable reactions of acetone such as aldol reaction are inevitable, and 4-chloro-4-methyl-2-pentanone, mesithyl oxide, 4-hydroxy-4-methyl-2-pentanone, etc., are produced. Therefore the recovery ratio of acetone is not necessarily high. In addition, degradation products of ketones cause coloration and a bad smell. It is thus difficult to establish industrial process for producing L-ascorbic acid using a ketone as a coexisting solvent.

OBJECTS OF THE INVENTION

The main object of the present invention is to provide an industrially advantageous process for producing L-ascorbic acid from 2-keto-L-gulonic acid.

This object as well as other objects and advantages of the present invention will become apparent to those skilled in the art from the following description.

SUMMARY OF THE INVENTION

In order to achieve the above objects, the present inventors have made extensive screening tests to find solvents that dissolve acids such as hydrochloric acid and are more stable than aliphatic ketones and produce L-ascorbic acid in yields equivalent to or higher than aliphatic ketones. As a result, it has been found that ethers are very effective. After further studies based on this finding, the present invention has been accomplished.

The present invention provide a process for producing L-ascorbic acid, which comprises reacting 2-keto-L-gulonic acid with an acid in an ether or an inert organic solvent containing an ether in the presence of water and a surfactant.

The process of the invention produces L-ascorbic acid in not less than 90% yield with little impurities and high recovery ratios of solvents. This process is thus particularly advantageous in industrial production.

DETAILED DESCRIPTION OF THE INVENTION

The ethers to be used in the invention are not specifically limited so long as they dissolve a certain amount or more of acids including gaseous acids. Examples thereof include cyclic or acyclic ethers containing an alkyl group having 1 to 10 carbon atoms. The cyclic ethers include tetrahydrofuran, dioxane, etc. The acyclic ethers include diethyl ether, n-propyl ether, diisopropyl ether, dibutyl ether, ethylene glycol dimethyl ether, diethylene glycol dimethyl ether, etc. The ethers must be present in a certain amount or more to maintain acids such as hydrochloric acid in the reaction system. The effective amount of the ether to be used is not less than 0.02 times by volume based on the inert organic solvent. Preferably, the amount of the ether is not less than 0.1 times by volume based on the inert organic solvent.

The inert organic solvents used in the invention mean solvents that do not react with the reagents or starting compound in the reaction system. Nonpolar or low polar organic solvents are preferred.

Examples of the inert organic solvents include aromatic hydrocarbons optionally substituted with halogen (e.g., fluorine, chlorine, bromine, iodine) or a lower alkyl group having 1 to 5 carbon atoms (e.g., methyl, ethyl), such as benzene, toluene, chlorobenzene, etc.; halogenated aliphatic hydrocarbons such as chloroform, ethylene dichloride, etc. These inert organic solvents can be used alone or in combination thereof. Preferred examples of the inert organic solvents include benzene and toluene. The amount of the inert organic solvent containing an ether is not specifically limited. From an economical point of view, it is normally 1 to 20 times by weight, preferably 2 to 5 times by weight, based on 2-keto-L-gulonic acid.

In one preferred embodiment of the invention, only the above cyclic or acyclic ether is used as a single solvent without using any inert organic solvent. In this case, a step of removing solvents and a step of recovering solvents are much more simple than those of a process using a mixed solvent of two or more different solvents. The process of the invention is thus very advantageous in industrial production.

The present process using an ether such as diisopropyl ether causes little decomposition with acids and inhibits production of by-products compared with prior art processes using an aliphatic ketone such as acetone as a coexisting solvent. In fact, comparison of Comparative Examples 1 with Examples 1 and 5 hereinafter clearly demonstrates this fact. That is, the recovery ratio of acetone is 83%, whereas the recovery ratio of ether is not less than 99% in the process of the invention using an ether.

The process of the invention is carried out in the presence of a surfactant. Examples of the surfactants include nonionic surfactants such as polyoxyethylene alkyl aryl ether, etc.; cationic surfactants such as trimethyltetradecylammonium chloride, trimethyldodecylammonium chloride, trimethylcetylammonium chloride, etc.; anionic surfactants such as alkyl aryl sulfonates, etc. These surfactants can be used alone or in combination thereof. The surfactant is preferably a cationic surfactant, more preferably a quaternary ammonium salt. The amount of the surfactant to be used is 0.01 to 10% by weight, preferably 0.05 to 3.0% by weight, based on 2-keto-L-gulonic acid.

In the invention, an acid is used as a catalyst. Examples of the acids include mineral acids such as hydrochloric acid, hydrobromic acid, sulfuric acid, phosphoric acid, etc.; sulfonic acids such as toluenesulfonic acid, methanesulfonic acid, etc.; carboxylic acids such as trifluoroacetic acid, etc.; strongly acidic ion-exchange resins such as Wofatit KPS (manufactured by VEB CHEMIEKOMBINAT BITTERFELD), etc. In particular, hydrochloric acid is preferred. The amount of the acid to be used is 0.5 to 2 mol, preferably 0.5 to 1.5 mol, per mol of 2-keto-L-gulonic acid. In order to keep the acid in higher concentrations in the reaction system, the acid may be bubbled as gas for the reaction. In the case of hydrochloric acid, for example, it is often preferred to bubble hydrogen chloride gas in addition to adding conc. hydrochloric acid.

For advantageous progress of the reaction, the amount of water to be used is 1.5 to 3.5 mol, preferably 1.8 to 3.0 mol, per mol of 2-keto-L-gulonic acid. Such water is normally supplied from water contained in the starting compound 2-keto-L-gulonic acid, and water in conc. hydrochloric acid. If necessary, water may be added to optimize the amount of water.

Under the above reaction conditions, the starting compound 2-keto-L-gulonic acid is converted to the corresponding lactone and then enol by the action of an acid catalyst to give L-ascorbic acid. In this case, because the amount of water in the reaction system increases with the progress of the reaction, if necessary, the amount of water may be adjusted by conventional dehydration operations such as azeotropic distillation. When the acid catalyst or the coexisting solvent is distilled away during the dehydration operations, the acid catalyst or the coexisting solvent can be supplemented.

The reaction temperature is 40° to 100° C., preferably 40° to 80° C., more preferably 50° to 70° C. The reaction time is normally 1 to 15 hours, preferably 2 to 8 hours.

The desired L-ascorbic acid can be separated from the reaction mixture and purified by per se known methods such as filtration, concentration, extraction, crystallization, chromatography, etc.

The process of the invention provides L-ascorbic acid in a high yield of not less than 90%. In addition, the process comprises simplified steps of removing and recovering solvents, provides a high recovery ratio of solvents, and produces very little impurities responsible for coloration. The process of the invention is thus industrially advantageous.

The following examples and comparative examples further illustrate the invention in detail, but are not to be construed to limit the scope of the invention. All the percents (%) used in the examples and comparative examples are percents by weight unless otherwise indicated.

EXAMPLE 1

An example using ethylene glycol dimethyl ether as the ether

A mixture of 2-keto-L-gulonic acid (250 g, 1.15 mol, content: 89.6%, water: 8.6%) and trimethylcetylammonium chloride (0.275 g) was stirred in toluene (960 ml), and 36% conc. hydrochloric acid (30.0 g) was added. At this time, the amount of water in the reaction system was calculated as 2.0 mol per mol of 2-keto-L-gulonic acid. This mixture was stirred at 60° C. for 1 hour, a solution of hydrogen chloride gas (30.0 g) in ethylene glycol dimethyl ether (130 g) was added, and the mixture was stirred at the same temperature for 5 hours. Then, about 1200 g of the solvent was distilled away under reduced pressure while continuously introducing toluene (850 ml). The residue was filtered to give crude crystals of L-ascorbic acid. The crude crystals were dissolved in water. Quantitative analysis of the solution by high performance liquid chromatography (HPLC) showed that the solution contained L-ascorbic acid (191.1 g, yield: 94.1%) and 2-keto-L-gulonic acid (2.7 g, residual ratio: 1.2%).

The quantitative analysis by HPLC was carried out under the following conditions. The same conditions were used in the quantitative analyses in Examples and Comparative Examples hereinafter.

Column: Aminex HPX-87H manufactured by Bio Rad

Eluent: 0.1M ammonium sulfate, pH 2.7 (adjusted with dilute sulfuric acid)

Temperature: Room temperature

Detection: Differential refractometer

Gas-chromatographic quantitative analysis of ethylene glycol dimethyl ether in the distillate and filtrate showed that the recovery ratio of the ethylene glycol dimethyl ether was 99%.

EXAMPLES 2 TO 4

Examples using tetrahydrofuran, diethylene glycol dimethyl ether and diisopropyl ether as the ethers Experiments were carried out in the same manner as that described in Example 1 except that the above ethers were used instead of ethylene glycol dimethyl ether.

The results are shown in Table 1.

TABLE 1

| Example No. | Ether | Ratio by volume * | Yield of L-ascorbic acid |
| --- | --- | --- | --- |
| 2 | Tetrahydrofuran | 0.15 | 91.9% |
| 3 | Diethylene glycol dimethyl ether | 0.13 | 92.9% |
| 4 | Diisopropyl ether | 0.18 | 92.1% |

* The ratio by volume represents the ratio of the ether to the inert organic solvent by volume.

EXAMPLE 5

Example using diisopropyl ether as a single solvent

A mixture of 2-keto-L-gulonic acid (125 g, 0.584 mol, content: 90.7%, water: 8.5%) and trimethylcetylammonium chloride (0.084 g) was stirred in diisopropyl ether (500 ml), and 36% conc. hydrochloric acid (18.0 g) was added. At this time, the amount of water in the reaction system was calculated as 2.1 mol per mol of 2-keto-L-gulonic acid. This mixture was stirred at 60° C. for 1 hour, a solution of hydrogen chloride gas (17.2 g) in diisopropyl ether (88 g)

was added, and the mixture was stirred at the same temperature for 5 hours. Then, about 900 g of the solvent was distilled away under reduced pressure while continuously introducing diisopropyl ether (1000 ml). The residue was filtered to give crude crystals of L-ascorbic acid. The crude crystals were dissolved in water. Quantitative analysis of the solution by HPLC showed that the solution contained L-ascorbic acid (95.8 g, yield: 93.1%) and 2-keto-L-gulonic acid (0.9 g, residual ratio: 0.8%). Quantitative analysis of diisopropyl ether in the distillate and filtrate showed that the recovery ratio was not less than 99%.

EXAMPLE 6

Example using dibutyl ether as a single solvent

A mixture of 2-keto-L-gulonic acid (125 g, 0.584 mol, content: 90.7%, water: 8.5%) and trimethylcetylammonium chloride (0.084 g) was stirred in dibutyl ether (500 ml), and 36% conc. hydrochloric acid (18.0 g) was added. At this time, the amount of water in the reaction system was calculated as 2.1 mol per mol of 2-keto-L-gulonic acid. This mixture was stirred at 60° C. for 1 hour, a solution of hydrogen chloride gas (17.2 g) in dibutyl ether (91 g) was added, and the mixture was stirred at the same temperature for 5 hours. Then, about 900 g of the solvent was distilled away under reduced pressure while continuously introducing toluene (1000 ml). The residue was filtered to give crude crystals of L-ascorbic acid. The crude crystals were dissolved in water. Quantitative analysis of the solution by HPLC showed that the solution contained L-ascorbic acid (92.4 g, yield: 90.0%) and no residual starting compound, i.e. 2-keto-L-gulonic acid.

EXAMPLE 7

Example using diisopropyl ether as the ether

A mixture of 2-keto-L-gulonic acid (125 g, 0.579 mol, content: 89.9%, water: 8.7%) and trimethylcetylammonium chloride (0.137 g) was stirred in toluene (240 ml) and diisopropyl ether (170 ml), and 36% conc. hydrochloric acid (15.6 g) was added. At this time, the amount of water in the reaction system was calculated as 2.0 mol per mol of 2-keto-L-gulonic acid. This mixture was stirred at 60° C. for 1 hour, a solution of hydrogen chloride gas (15.5 g) in diisopropyl ether (70 ml) was added, and the mixture was stirred at the same temperature for 5 hours. Then, about 500 g of the solvent was distilled away under reduced pressure while continuously introducing toluene (720 ml). The residue was filtered to give crude crystals of L-ascorbic acid. The crude crystals were dissolved in water. Quantitative analysis of the solution by HPLC showed that the solution contained L-ascorbic acid (93.8 g, yield: 92.0%) and 2-keto-L-gulonic acid (0.3 g, residual ratio: 0.3%).

COMPARATIVE EXAMPLE 1

Example using acetone as a coexisting solvent

A mixture of 2-keto-L-gulonic acid (250 g, content: 89.6%, water: 8.6%) and trimethylcetylammonium chloride (0.275 g) was stirred in a mixed solvent of toluene (960 ml) and acetone (24 ml), and 35% conc. hydrochloric acid (30.0 g) was added. This mixture was stirred at 60° C. for 1 hour, a solution of hydrogen chloride gas (30.0 g) in acetone (116 g) was added, and the mixture was stirred at the same temperature for 5 hours. Then, about 1200 g of the solvent was distilled away under reduced pressure while continuously introducing toluene (850 ml). The residue was filtered to give crude crystals of L-ascorbic acid. The crude crystals were dissolved in water. Quantitative analysis of the solution by HPLC showed that the solution contained L-ascorbic acid (190.0 g, yield: 93.5%) and 2-keto-L-gulonic acid (2.7 g, residual ratio: 1.2%).

Gas-chromatographic quantitative analysis of the acetone in the distillate and filtrate showed that the recovery ratio of acetone was 83%.

COMPARATIVE EXAMPLE 2

Example using t-butanol as a coexisting solvent

A mixture of 2-keto-L-gulonic acid (250 g, content: 89.6%, water: 8.6%) and trimethylcetylammonium chloride (0.275 g) was stirred in toluene (960 ml), and 35% conc. hydrochloric acid (30.0 g) was added. This mixture was stirred at 60° C. for 1 hour, a solution of hydrogen chloride gas (30.0 g) in t-butanol (130 g) was added, and the mixture was stirred at the same temperature for 5 hours. Then, about 1200 g of the solvent was distilled away under reduced pressure while continuously introducing toluene (850 ml). The residue was filtered to give crude crystals of L-ascorbic acid. The crude crystals were dissolved in water. Quantitative analysis of the solution by HPLC showed that the solution contained L-ascorbic acid (50.6 g, yield: 25.0%) and 2-keto-L-gulonic acid (146.8 g, residual ratio: 65.7%).

What is claimed is:

1. A process for producing L-ascorbic acid, which consists essentially of reacting 2-keto-L-gulonic acid with an acid in an ether or an inert organic solvent containing an ether in the presence of water and a surfactant.

2. The process according to claim 1, wherein the ether is a cyclic or acyclic ether containing an alkyl group having 1 to 10 carbon atoms.

3. The process according to claim 1, wherein the acid is hydrochloric acid.

4. The process according to claim 1, wherein the surfactant is a quaternary ammonium salt.

5. The process according to claim 1, wherein the amount of the water present is 1.5 to 3.5 mol per mol of 2-keto-L-gulonic acid.

6. The process according to claim 1, wherein the amount of the ether is not less than 0.02 times by volume based on the inert organic solvent.

7. The process according to claim 1, wherein 2-keto-L-gulonic acid is reacted with an acid in an ether in the presence of water and a surfactant.

* * * * *